(12) United States Patent
Casutt

(10) Patent No.: US 6,358,152 B2
(45) Date of Patent: Mar. 19, 2002

(54) MEDICAL/TECHNICAL TOOL HOLDER APPARATUS WITH TORQUE LIMITATION AND A SHEAR BODY FOR AN APPARATUS OF THIS KIND

(75) Inventor: Simon Casutt, Gossau (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/742,158

(22) Filed: Dec. 19, 2000

(30) Foreign Application Priority Data

Dec. 20, 1999 (EP) .............................. 99811172

(51) Int. Cl.[7] .................................. F16D 9/06
(52) U.S. Cl. .......................................... 464/32; 464/34
(58) Field of Search .............................. 464/30, 32, 33, 464/34, 37, 41

(56) References Cited

U.S. PATENT DOCUMENTS

| | | | | |
|---|---|---|---|---|
| 2,989,857 A | * | 6/1961 | Helland et al. | 464/30 |
| 3,942,338 A | * | 3/1976 | Furlette et al. | 192/56 |
| 4,218,896 A | * | 8/1980 | van der Lely | 64/28 R |
| 4,344,306 A | * | 8/1982 | Citron | 464/34 |
| 4,572,041 A | * | 2/1986 | Rissmann | 81/477 |
| 5,158,458 A | | 10/1992 | Perry | |
| 5,242,154 A | * | 9/1993 | Schmidt | 254/323 |
| 5,347,894 A | | 9/1994 | Fischer | |
| 5,368,480 A | | 11/1994 | Balfour | |
| 5,733,122 A | * | 3/1998 | Gordon | 433/172 |
| 5,746,298 A | * | 5/1998 | Krivec et al. | 192/48.3 |
| 6,220,415 B1 | * | 4/2001 | Cosenza | 192/56.1 |

* cited by examiner

Primary Examiner—Lynne H. Browne
Assistant Examiner—Kenn Thompson
(74) Attorney, Agent, or Firm—Townsend and Townsend and Crew LLP

(57) ABSTRACT

The medical/technical tool holder apparatus (2) with torque limitation comprises a receiver (5) for at least one shear body (7) and a shearing means (10a) which is rotatably connected to the receiver (5) and which is arranged in such a manner with respect to a shear body (7) located in the receiver (5) that the shearing means (10a) contacts the shear body (7) as soon as a torque acts on the shearing means (10a), with the shearing means (10a) and the shear body (7) being mutually matched and arranged in such a manner that the shearing means (10a) at least partly severs the shear body (7) when a specific torque is exceeded.

22 Claims, 6 Drawing Sheets

Figure 3A:
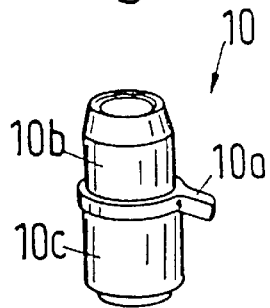

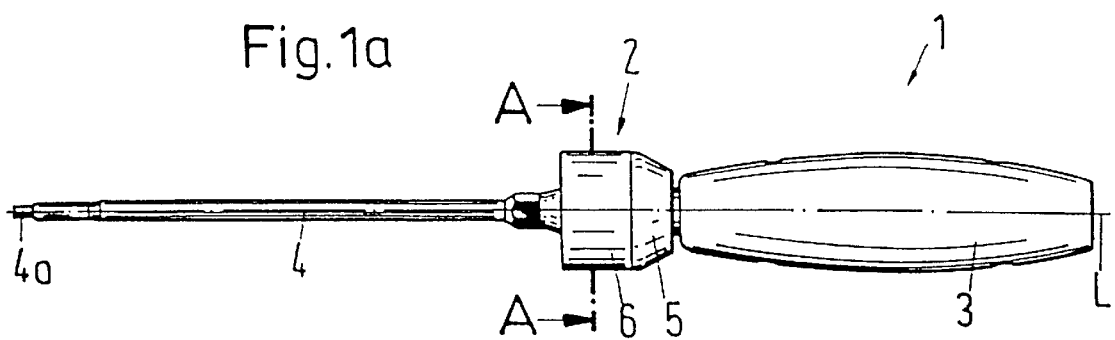
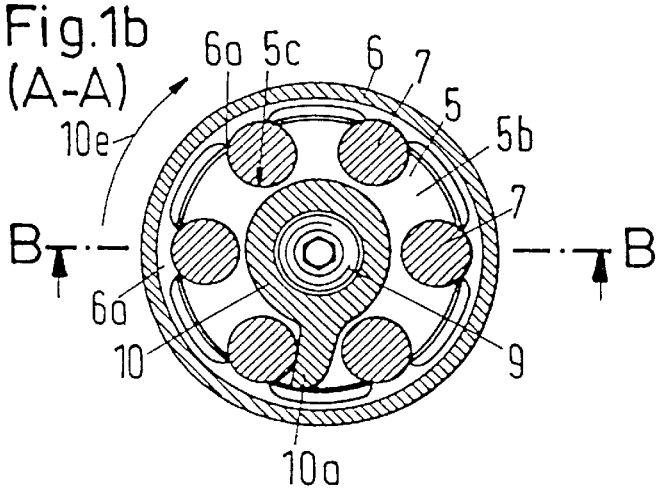
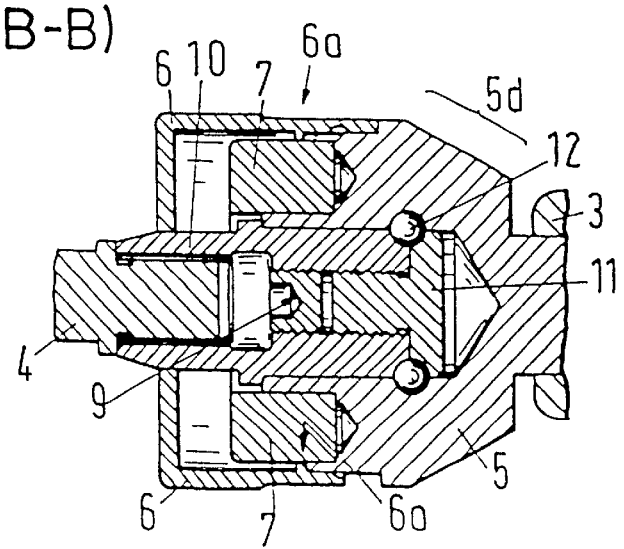

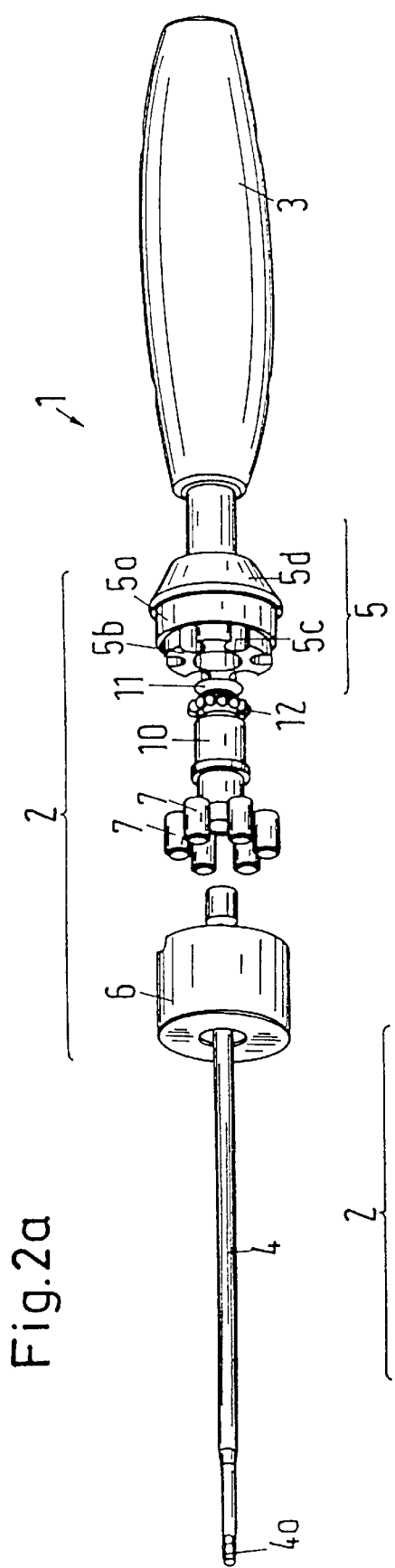
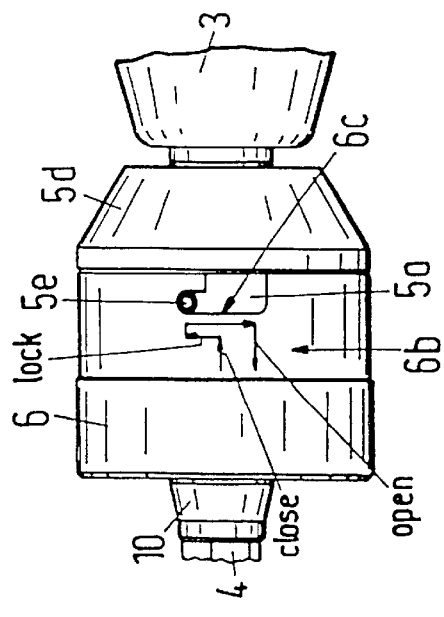
Fig.2a
Fig.2b (C-C)

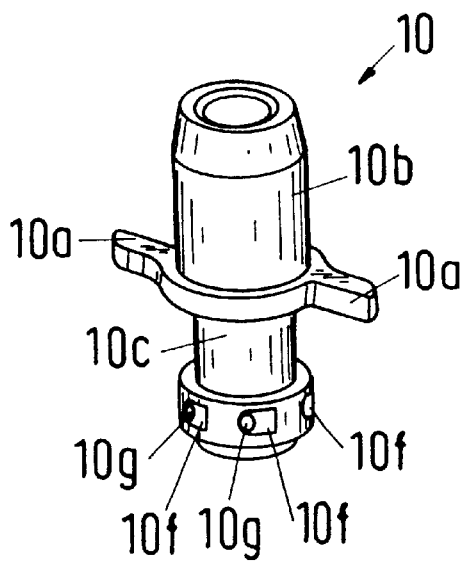
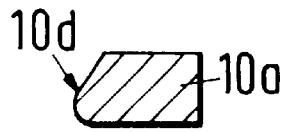
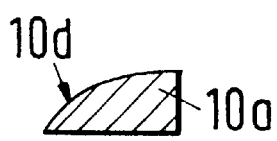
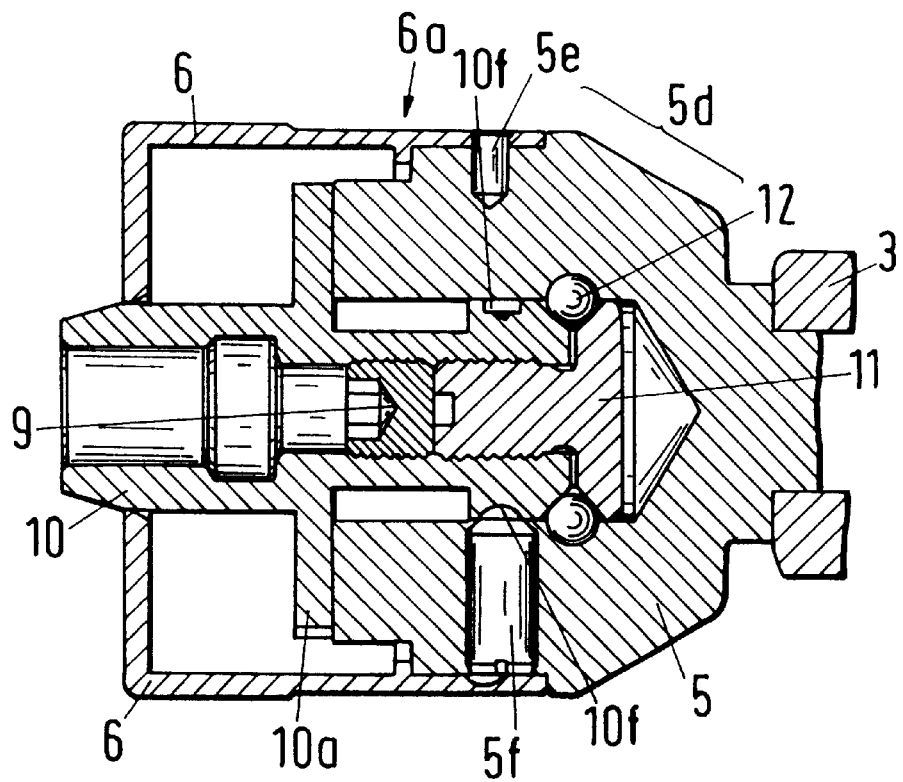

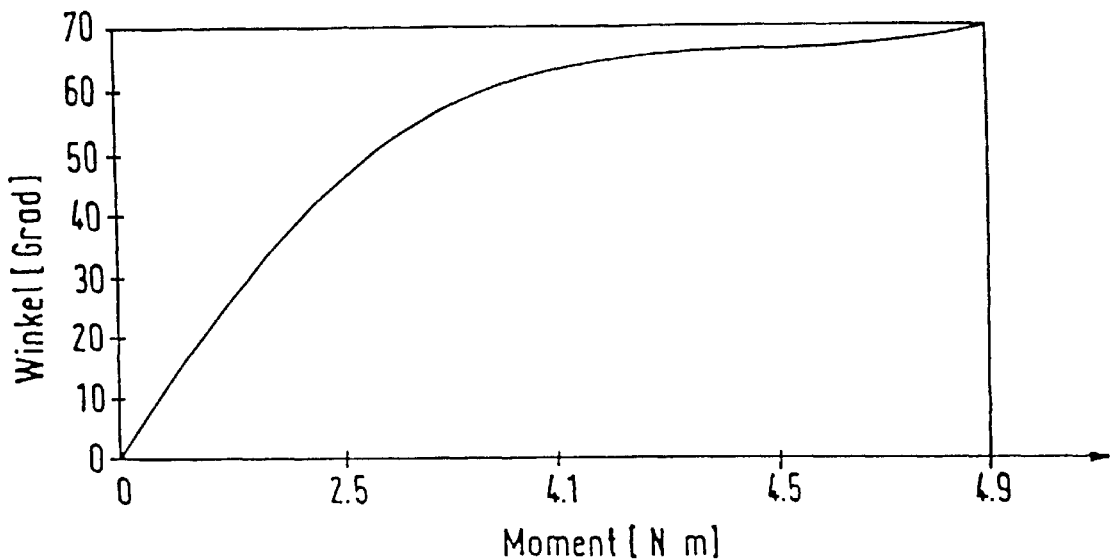
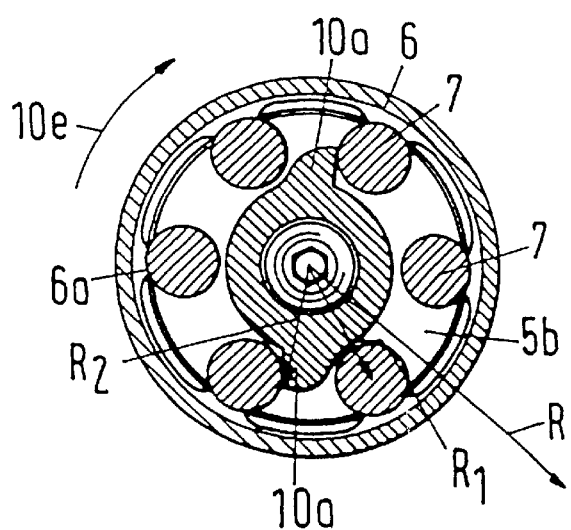

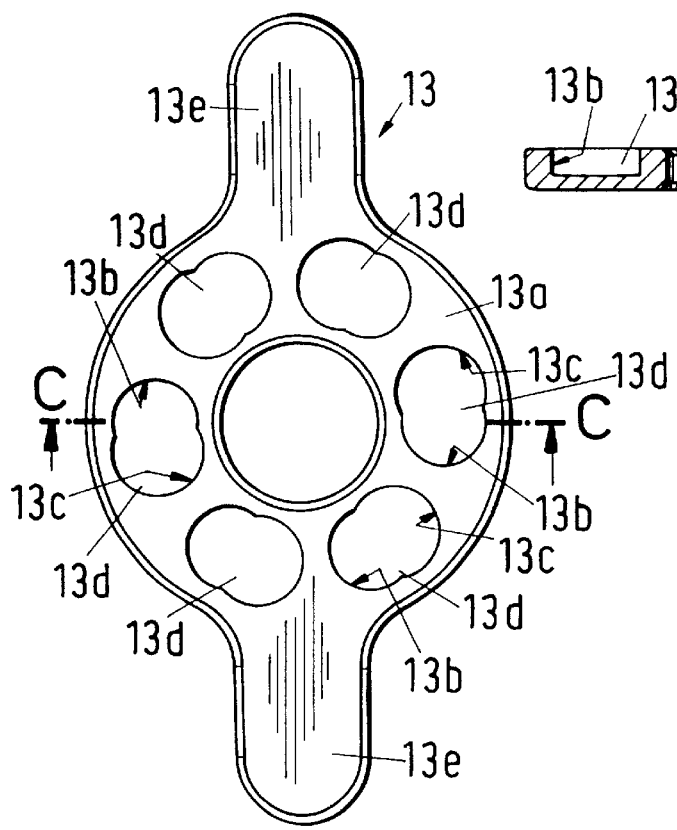
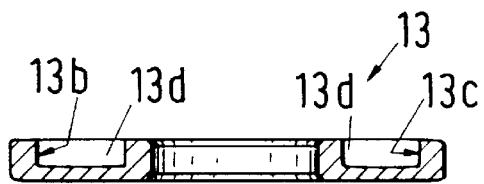
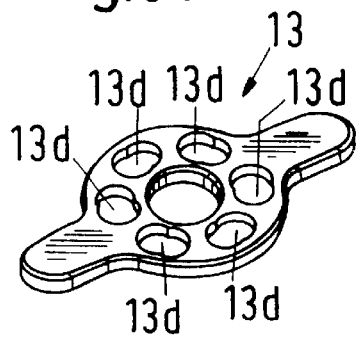
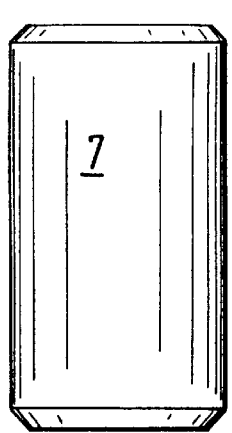
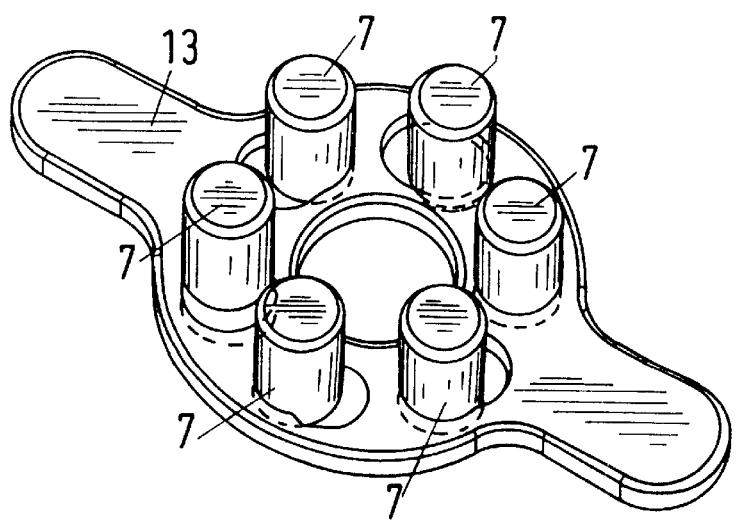

MEDICAL/TECHNICAL TOOL HOLDER APPARATUS WITH TORQUE LIMITATION AND A SHEAR BODY FOR AN APPARATUS OF THIS KIND

The invention relates to a medical/technical tool holder apparatus with torque limitation in accordance with the preamble of claim 1. The invention further relates to a shear body for a medical/technical tool holder apparatus with torque limitation in accordance with the preamble of claim 14. The invention further relates to a kit for a medical/technical tool holder apparatus with torque limitation in accordance with the preamble of claim 19.

A large number of torque transmitting couplings which transfer only a limited torque is known from mechanics. Couplings of this kind are also designated as overload couplings.

Disadvantageous in couplings of this kind is that they are not suitable for medical/technical uses, for example when built into instruments for surgical operations in humans, since the maximum torque which can be achieved is relatively imprecise, and the maximum torque which can be achieved is subject to long-term changes.

The object of the present invention is to create a medical/technical tool holder apparatus with torque limitation which has a relatively exact maximum torque, with the maximum torque being reproducible even in the long run, for example after multiple steam sterilizations.

This object is satisfied by a medical/technical tool holder apparatus with torque limitation having the features of claim 1. Subordinate claims 2 to 12 relate to further, advantageous embodiments of medical/technical tool holder apparatuses with torque limitation. The object is further satisfied by a shear body in accordance with claim 14, which is designed to be adapted for use in the medical/technical tool holder apparatus in accordance with the invention. Subordinate claims 15 to 18 relate to further advantageously designed shear bodies.

The object is satisfied in particular by a medical/technical tool holder apparatus with torque limitation which comprises a receiver for at least one shear body and a shearing means which is rotatably connected to the receiver and which is arranged relative to a shear body located in the receiver in such a manner that the shearing means contacts the shear body at least when a torque acts on the shearing means, with the shearing means and the shear body being mutually matched and arranged in such a manner that the shearing means at least partly severs the shear body when a specific torque is exceeded.

In a preferred embodiment, the medical/technical tool holder apparatus in accordance with the invention is connected on the one side to a handle and on the other side to a tool and forms in this manner a medical/technical instrument, for example a surgical instrument. In a preferred embodiment the handle is designed to be elongate and in this defines a longitudinal axis about which the instrument is rotated together with the tool, with the tool holder apparatus, which is arranged between the handle and the tool, limiting the maximum torque to be transmitted. For greater torques, for example for torques greater than 5 Nm, the handle can also be designed as a T-grip.

The medical/technical tool holder apparatus in accordance with the invention has the advantage that the maximum torque which can be transmitted can be relatively precisely defined through the use of a shear body in combination with a shearing means. The shear body is destroyed through the action of the shearing means and must be replaced after the use of the tool holder apparatus. The shearing means has a low wear and can, where appropriate, likewise be replaced. The medical/technical tool holder apparatus in accordance with the invention therefore has the advantage that the maximum torque which can be transmitted is relatively exactly reproducible over a relatively long time interval of, for example, a year or even several years. In addition no calibration of the tool holder apparatus is required.

The shearing means come into contact with the shear body at the latest when the handle is rotated, with the shearing means penetrating into the shear body with increasing torque and partly or completely severing it when a specific torque is exceeded. A severed shear body is destroyed and must be replaced. In an advantageous embodiment the tool holder apparatus in accordance with the invention has a receiver for a plurality of shear bodies, for example a receiver for six shear bodies, so that the shear body is severed a number of times in succession when a specific torque is exceeded, but the shear bodies must be replaced only when all shear bodies located in the instrument have been destroyed.

The medical/technical tool holder apparatus in accordance with the invention enables for example a screw such as a stud screw or a bone screw to be tightened with a precisely pre-set torque during implanting.

The tool holder apparatus in accordance with the invention has the advantage that maximum torques of different magnitude can be pre-set depending on the requirement. The maximum torque for the severing of a shear body is determined by:

the material properties of the shear body, the geometrical design of the shear body, the geometrical design of the shearing means, with the shearing means preferably having a blade, the geometry of which can be designed in a large number of shapes, the effective lever arm of the shearing means, the degree of the severing of the shear body, partial or complete.

Through a suitable combination of these parameters, a large number of different and precisely reproducible maximum torques can be achieved. In a preferred embodiment the same shearing means is always used, with shear bodies having different material properties and/or different geometrical designs being used, so that the maximum torque amounts to, for example, 4 Nm, 6 Nm or 10 Nm, depending on the respective shear body. In a preferred embodiment these shear bodies have a color coding, with shear bodies of the same color yielding the same maximum torque. The tool holder apparatus in accordance with the invention thus has the advantage that the maximum torque achievable can be varied within a broad range using the same apparatus, in which a corresponding shear body is inserted into the receiver depending on the required maximum torque. Especially in the implanting of an orthopedic implant such as a hip joint pan, the maximum permissible torque can depend, for example, on the size of the implant chosen. The tool holder apparatus in accordance with the invention enables a surgeon or an assistant to set the maximum torque of the instrument during an operation by the corresponding shear bodies being inserted into the receiver. A set of different shear bodies must be available in sterilized form for this.

A surgical instrument comprising the medical/technical tool holder apparatus in accordance with the invention can, for example, be designed as a torque limitation screwdriver.

The medical/technical tool holder apparatus in accordance with the invention is manufactured of a sterilizable material, in particular metal, in a preferred embodiment, so that the shear body can be removed from the apparatus after an operation, the apparatus is sterilized and can then be used for further operations.

The tool holder apparatus in accordance with the invention can be assembled for a great variety of release moments without altering the external geometry of the tool holder apparatus or of the shear pin. The tool holder apparatus in accordance with the invention can be assembled in a module-like way taking into account the respective release moment required so that an instrument having the required release moment is available with a few changes, for example replacing a single blade with a double blade, or by the use of a blade with a sharp or blunt form.

Figure 3B:
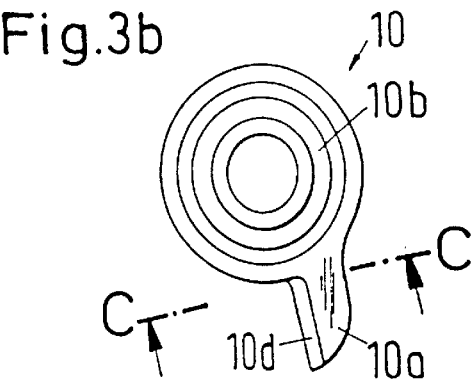
Figure 4:
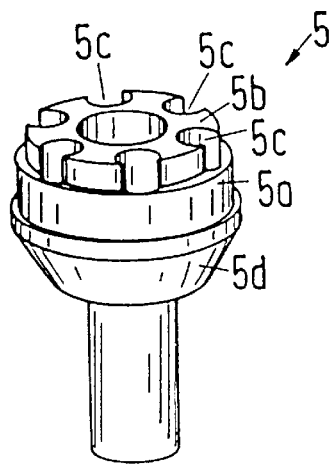
Figure 3C:
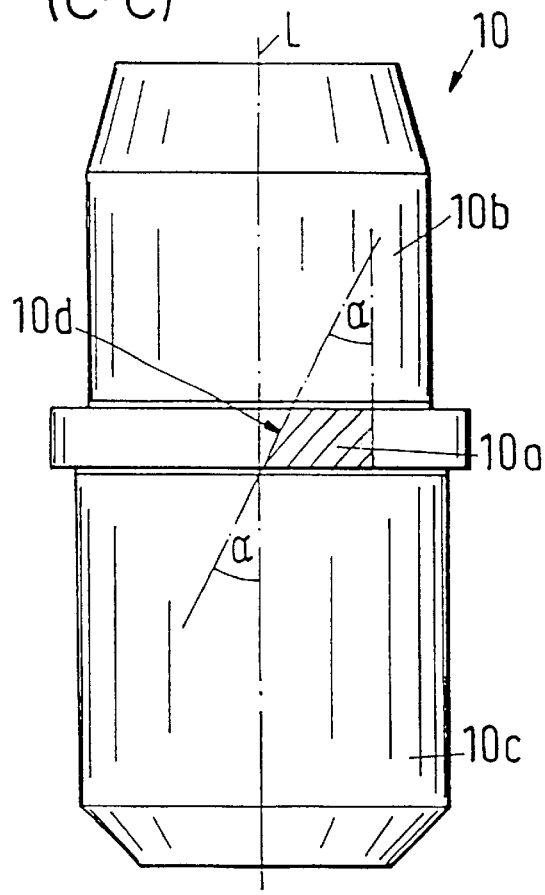
Figure 7:
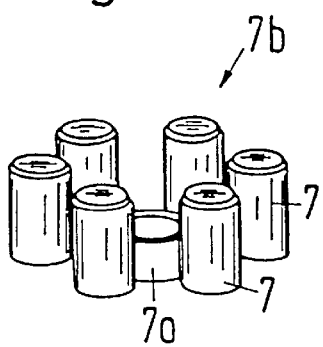

The invention will be described in detail with reference to several exemplary embodiments. Shown are:

FIG. 1a a side view of a medical/technical tool holder apparatus which is built into a medical/technical instrument;

FIG. 1b a cross-section through the tool holder apparatus in accordance with FIG. 1a along the section line A—A;

FIG. 1c a longitudinal section through the tool holder apparatus in accordance with FIG. 1b along the section line B—B;

FIG. 2a an exploded view of the tool holder apparatus;

FIG. 2b a detail view of the interlock of a tool holder apparatus;

FIG. 3a a view of a shaft comprising a shearing means;

FIG. 3b a plan view of the shaft in accordance with FIG. 3a;

FIG. 3c a side view of the shaft in accordance with FIG. 3b and a section through the shearing means along the section line C—C;

FIGS. 3d, 3e a section through further embodiments of shearing means;

FIG. 4 a view of a receiver;

FIG. 5 an illustration of the relationship between the angle α of the blade and the maximum torque which can be achieved;

FIG. 6 a cross-section along the section line A—A with a blade which is designed to be shorter;

FIG. 7 a ring consisting of six individual shear bodies or of shear bodies which are firmly connected to one another.

FIG. 8a a further embodiment of a shaft comprising a shearing means and recesses for a locking device;

FIG. 8b a longitudinal section through a further embodiment of a tool holder apparatus with a free wheel mechanism;

FIG. 9a a plan view of a holder apparatus for shear pins;

FIG. 9b a section through the holder apparatus in accordance with FIG. 9a along the section line C—C;

FIG. 9c a perspective view of the holder apparatus;

FIG. 10 a side view of a shear pin;

FIG. 11 a perspective view of a holder apparatus having inserted shear pins.

FIG. 1a shows the side view of a surgical instrument 1 comprising a medical/technical tool holder apparatus 2 with torque limitation. The tool holder apparatus 2 comprises a receiver 5 which at the same time forms a first sub-housing, a second sub-housing 6 and a shaft 10 which is rotatably journalled about a common longitudinal axis L in the receiver 5, with the shaft 10 having a mount for a tool 4. A handle 3, which extends in the direction of the longitudinal axis L, is secured to the receiver 5. The releasable tool 4, which extends in the direction of the longitudinal axis L and at the tip 4a of which a hexagon for accommodating a hexagon screw is arranged, is secured to the shaft 10.

FIG. 1b shows the inner construction of the tool holder apparatus 2 as a cross-section along the section line A—A. The receiver 5 comprises a holder 5b with six holder openings 5c which are regularly distributed over the periphery and in each of which a cylindrically designed shear body 7 is arranged. A shaft 10 which extends in the direction of the longitudinal axis L has a shearing means 10a which projects radially with respect to the longitudinal axis L. The shaft 10 and the shearing means 10a are rotatably journalled in the receiver 5 about the longitudinal axis L. The shearing means 10a and the shear bodies 7 are mutually arranged in such a manner that the shearing means 10a lies between the shear bodies 7 and is hindered with respect to a rotational movement in the relative direction of rotation 10e. When a specific torque is exceeded the shear body 7, at which the shearing means 10a lies in contact, is severed by the latter. Therefore, during the tightening of a screw which is being screwed in by means of the instrument 1 a predetermined, maximum torque can not be exceeded. The illustrated instrument 1 permits a maximum of six screws to be tightened one after the other with a given torque. Each time that a specific torque is reached, a single shear body 7 is severed so that after six procedures of this kind all shear bodies 7 are severed and must be replaced.

The longitudinal section through the instrument 1 along the line B—B which is illustrated in FIG. 1c shows the receiver 5 with the shear bodies 7 which are arranged therein. The receiver 5 is firmly connected to the handle 3. In the receiver 5 the shaft 10 and the shaft lock 11 are rotatably journalled via a ball bearing 12, with the shaft 10 and the shaft lock 11 being held together by a counter-screw 9. The tool 4 is releasably, for example pluggably or screwably, connected to the shaft 10. The sub-housing 6 is displaceable in the longitudinal direction L and can be firmly connected to the receiver 5 via a connection, for example a snap connection.

The sub-housing 6 is partly passed over an outer surface 5a of the receiver 5 and surrounds in this manner the inner space which is formed by the receiver 5, the shaft 10 and the sub-housing 6. This inner space is preferably sealed off against the outside in that a seal is formed between the sub-housing 6 and the shaft 10 and/or between the shaft 10 and the tool 4 respectively, so that no liquid, in particular no water or no blood, can penetrate into the inner space. Likewise no loose objects which are possibly located in the inner space can arrive at the outside.

FIG. 2a shows in an exploded view the individual constituents of the instrument 1 in detail. The instrument 1 consists of the tool 4, the handle 3 and the medical/technical tool holder apparatus 2 which connects these two and which comprises the receiver 5 with the holder 5b, the shaft 10 with the shaft lock 11 and the ball bearing 12 as well as a sub-housing 6. The shear bodies 7, which are considered as consumable material, can be inserted into the holder 5b.

FIG. 2b shows an exemplary embodiment of an interlocking device in order to releasably and firmly connect the receiver 5 and the second sub-housing 6 to one another. The receiver 5 has a cylindrical part 5a with a smooth surface at which a pin 5e is arranged to project in the radial direction with respect to the part 5a. The second sub-housing 6 has a cut-out 6c which is designed to be matched to the arrangement of the pin 5e. A marking 6b which is applied to the surface of the second sub-housing 6 represents the required movements in order to connect or to release the parts 5, 6. Through a movement in the "close" direction the second sub-housing 6 is pushed over the cylindrical part 5a until the pin 5e abuts at the cut-out 6c. The receiver 5 is then rotated in the "lock" direction until the pin 5e is in the position illustrated in FIG. 2b. In this position the receiver 5 and the second sub-housing 6 are firmly connected and the holder blades 6a are in engagement with the shear pins 7. The "open" marking comprises two directions which extend perpendicular to one another. In order to release the connection the receiver 5 is first rotated in the "open" direction and then the second sub-housing 6 is drawn off in the "open" direction (perpendicular to the direction of rotation). In FIG. 2b it can be seen that a slight rotation of the receiver 5 in the "open" direction already suffices in order to remove the pin 5e from the cut-out 6c. As a result of the position of the holding blades 6a, the shear pins 7 are either removed at the same time from the holder 5b or they remain in the holder 5b during the drawing off of the second sub-housing 6, depending on how far the receiver 5 is rotated in the "open" direction during the opening.

FIG. 3a shows the shaft 10, which is formed in a single piece, with an upper shaft part 10b, a lower shaft part 10c and the projecting shearing means 10a in detail. In the plan view of FIG. 3b the upper shaft part 10b, the shearing means 10a and its blade 10d can be seen. The side view in accordance with FIG. 3c shows the shaft 10, which extends in the longitudinal direction L, with the upper shaft part 10b and the lower shaft part 10c. The shearing means 10a is illustrated in a section along the line C—C and shows an areally extending blade 10d which extends at an inclination by an angle α with respect to the longitudinal axis L. The blade 10d can also be formed with many other geometrical shapes in addition to that of a planar cutting surface and can have, for example, as shown in FIGS. 3d and 3e, a partly rounded or elliptical cutting surface.

FIG. 4 shows a perspective view of the receiver 5 with an outer thread 5a, a holder 5b with holding openings 5c for the shear body 7 and an outer housing 5d. The shear bodies 7 or shear pins 7 respectively, which are, for example, designed cylindrically, can be inserted individually into the receiver 5. Only as many shear bodies 7 as necessary are to be inserted. In the illustrated exemplary embodiment in accordance with FIGS. 1a, 1b, 1c the shear bodies 7 are inserted into the receiver 5, then the sub-housing 6 is moved in the longitudinal direction L until the latter is passed over the surface 5a. Then the sub-housing 6 is rotated slightly in the direction 10e until the sub-housing 6 snaps into a non-illustrated latching device and is thereby held firmly in its position. The housing 6 comprises six holding blades 6a which are distributedly arranged over the periphery, which project radially inwardly and which penetrate during the rotation in the direction 10e into the shear bodies 7 and fix the latter in their position. Through this it is ensured that the shear bodies 7 do not move freely in the inner space of the torque limitation apparatus 2 during the use of the tool 1. In an advantageous embodiment the shear bodies 7 are only partly severed by the shearing means 10a so that no loose parts, in particular no larger loose parts, are produced through the shearing action.

FIG. 7 shows a further exemplary embodiment of a shearing means 7b which consists of six shear bodies 7 which are firmly connected to one another via a holding ring 7a. The entire shearing means 7b can be inserted with a handle into the receiver 5. The shearing means 7b could also be designed in such a manner that the shear bodies 7 are connected to the holding ring 7a only slightly or not at all.

FIG. 5 shows for a specific material and for a specific geometrical design of the shear body 7 the relationship between the angle α of the blade 10d of the shearing means 10a which is illustrated in FIG. 3c and the resulting maximum torque. Through a corresponding choice of the angle α the maximum torque can be set relatively precisely. For this a plurality of shafts 10 with blades 10d of different angles α can be stored in a kit for the tool 1 so that the blade 10d which is required for achieving a desired maximum torque can be inserted into the receiver 5. If a tool 1 with the same shearing means 10a or with the same angle α respectively is continually used, then the maximum torque can be varied in that different shear bodies 7 are available for insertion into the receiver 5, with these shear bodies 7 for example consisting of different material or having a different density or a different geometry. Further possibilities of influencing the maximum torque consist, as illustrated in FIG. 6, in varying the radial length R2 of the shearing means 10a and/or using a plurality of shearing means 10a at the same time. In the illustrated exemplary embodiment the radial length R2 is less than the distance R1 of the center of the shear body 7 from the center of rotation of the shearing means 10a. The shear body 7 is therefore only partly severed by the shearing means 10a. Shearing means 10a can be equipped with one blade 10d or, as illustrated in FIG. 6, with two blades 10d, or for example with three blades 10d. Through a corresponding variation of the number of the blades 10d it was possible for example to achieve the following maximum torques:

TABLE 1

The relationship between the number of blades and the maximum torque

| Number of blades | Maximum torque | Maximum number of uses with 6 shear pins |
| --- | --- | --- |
| 1 | 4 Nm | 6x |
| 2 | 8 Nm | 3x |
| 3 | 12 Nm | 2x |

Tab. 1 The relationship between the number of blades and the maximum torque.

In this manner the maximum torque can be varied through a corresponding choice of the number of blades 10d of the shearing means 10a. Identical shear pins 7 are preferably used for this. Further different values of the maximum torque can be achieved for example through differently designed blades 10d, or through differently designed shear pins 7.

The shaft 10 shown in FIG. 8a has, in distinction to the embodiment shown in FIG. 3a, two shearing means 10a arranged opposite one another. Furthermore, the end section of the lower shaft part 10c has ramp-like recesses 10f, each having a circular depression 10g, arranged at intervals in the direction of the periphery.

FIG. 8b shows a further embodiment of a tool holder apparatus in a longitudinal section. The same reference numerals refer to the same elements in FIGS. 1c and 8b. In contrast to the section shown in FIG. 1c, the section in FIG. 8b is taken such that the latter does not extend through the shear pins 7, but completely through the metal receiver 5. The shear pins 7 normally located in the receiver 5 are not shown in FIG. 8b. The shaft 10 is designed as in FIG. 8a. The tip of a pin 5f resiliently arranged in the receiver 5 presses into the ramp-like recess 10f, that is into the circular depression 10g, and in this way effects a free-wheeling in the one direction of rotation. When the handle 3 is turned clockwise, the torque is transmitted via the shear pins 7 and the shearing means 10a to the shaft 10 or to the tool 4 connected to the shaft 10. When the handle 3 is turned counter-clockwise, the transmission of the torque is made via the resilient pin 5f and the circular depression 10g directly onto the shaft 10 and the tool 4 connected thereto. This arrangement has the advantage that when a screw is tightened, the maximum torque is limited, whereas the pin 5*f* allows a limited torque to be transmitted from the handle 3 to the tool 4 in order to release the screw. The amount of torque which can be transferred at a maximum in this way can be from very small to very large in dependence on the respective design selected in order to generate in particular a torque which is sufficient to release a screw.

FIG. 9*a* shows a plan view of a holder apparatus 13 for shear pins 7. The holder apparatus 13 has a circular carrier 13*a* with two tabs 13*e*, with six recesses 13*d* being evenly spaced in the direction of the periphery in the carrier. Each recess 13*d* has a bore 13*b* with a smaller diameter and, arranged offset in the direction of the periphery, a bore 13*c* of a greater diameter. FIG. 9*s* shows a section through the holder apparatus 13 along the line C—C. FIG. 9*c* shows a perspective view of the holder apparatus 13.

FIG. 10 shows a side view of a shear pin 7.

FIG. 11 shows a holder apparatus 13 with six inserted shear pins 7. To join the shear pins 7 to the holder apparatus 13, they are first inserted into the bore 13 *c* of greater diameter and then moved against the bore 13*b* of smaller diameter so that a force fit results and the shear pin 7 is held thereby. To refill the shear pins in the receiver 5, these are first arranged in the holder apparatus 13 as shown in FIG. 11. The shear pins 7 held in this way are then inserted jointly into the respective holder openings 5*c* of the receiver 5. The holder apparatus 13 is then turned slightly with respect to the receiver 5 so that the force fit is released by the bore 13*c* of greater diameter surrounding the shear pins 7. The holder means 13 can now be raised up with the shear pins 7 remaining in the holder openings 5*c*.

(Text for FIG. 5: Winkel [Grad]=Angle [degrees]
  Moment [N m]=Torque [N m])
  What is claimed is:

1. Medical/technical tool holder apparatus (2) with torque limitation, comprising a receiver (5) for holding at least one shear body (7) and a shearing means (10*a*) which is rotatably connected to the receiver (5), with the shearing means (10*a*) and the receiver (5) being mutually matched in such a manner that the shearing means (10*a*) contacts a held shear body (7), at least when a torque acts on the shearing means (10*a*); in that the shearing means (10*a*) has at least one blade (10*d*); in that the blades (10*d*) are arranged such that they act on the shear body (7); and in that the shearing means (10*a*) at least partly severs the shear body (7) when a specific torque is exceeded.

2. Medical/technical tool holder apparatus (2) in accordance with claim 1, characterized in that the receiver (5) can be connected to a handle (3) and the shearing means (10*a*) can be connected to a tool (4); or in that the receiver (5) can be connected to the tool (4) and the shearing means (10*a*) can be connected to the handle (3).

3. Medical/technical tool holder apparatus (2) in accordance with claim 1, characterized in that the shear body (7) consists of a thermoplastic such as polyethylene, UHMW polyethylene or of metal.

4. Medical/technical tool holder apparatus (2) in accordance with claim 1, characterized in that the receiver (5) is designed for the mounting of a plurality of shear bodies (7), in particular of six shear bodies (7).

5. Medical/technical tool holder apparatus (2) in accordance with claim 1, characterized in that, together with a removable housing part (6), the receiver (5) forms a cavity within which the shearing means (10*a*) and the shear body (7) are arranged.

6. Medical/technical tool holder apparatus (2) in accordance with claim 5, characterized in that removable housing part (6) has holding means (6*a*) which are arranged on its inner side and which are intended for the holding of the shear body (7).

7. Medical/technical tool holder apparatus (2) in accordance with claim 1, characterized in that the shearing means (10*a*) is firmly connected to a shaft (10) which is rotatably journalled about an axis of rotation (10*f*).

8. Medical/technical tool holder apparatus (2) in accordance with claim 7, characterized in that the blade (10*d*) has an extent which is inclined with respect to the axis of rotation (10*f*) by an angle α, with the value of the angle α lying in particular between 0 degrees and 89 degrees.

9. Medical/technical tool holder apparatus (2) in accordance with claim 1, characterized in that the blade (10*d*) has an at least partly rounded cutting surface.

10. Medical/technical tool holder apparatus (2) in accordance with claim 1, comprising a blade (10*d*), the length extending radially to the axis of rotation (10*f*) of which amounts to between 5 mm and 20 mm.

11. Medical/technical tool holder apparatus (2) in accordance with claim 1, characterized in that at least the receiver (5) and the shear body (7), preferably also the tool (4) and the handle (3), consist of a sterilizable metal.

12. Medical/technical tool holder apparatus (2) in accordance with claim 1, characterized in that it comprises a free-wheel mechanism which is formed such that the shearing means (10*a*) is rotationally mounted in the one direction of rotation with respect to the receiver (5); and in that the shearing means (10*a*) is locked in the opposed direction of rotation with respect to the receiver (5).

13. Medical/technical device (1) comprising a tool holder apparatus (2) in accordance with claim 1.

14. Shear body (7) designed for use in a medical/technical tool holder apparatus (2) in accordance with claim 1.

15. Shear body (7) in accordance with claim 14, characterized in that the shear body (7) is designed as a cylindrical body.

16. Shear body (7) in accordance with claim 14, characterized in that the latter comprises a plurality of individual shear bodies (7) which are connected to one another.

17. Shear body (7) in accordance with claim 14, characterized by a plurality of shear bodies (7) of different materials and/or of different density, with similarly acting shear bodies (7) being coded identically.

18. Shear body (7) in accordance with claim 17, characterized in that the latter are coded with colors; and in that similarly acting shear bodies (7) have the same code.

19. Kit for a medical/technical tool holder apparatus (2) with torque limitation in accordance with claim 1, comprising
  a plurality of receivers (5) for holding at least one shear body (7) and/or for holding the shear body (7) at different distances from the center of rotation,
  a plurality of shear bodies (7) of different shape and/or different materials and/or different densities,
  a plurality of shearing means (10*a*) which are designed as blades, with the blades having a different length and/or the blades (10*d*) having a differently inclined angle α with respect to the axis of rotation (10*f*), and with each shearing means (10*a*) having one or more blades (10*d*).

20. Kit for a medical/technical tool holder apparatus (2) with torque limitation in accordance with claim 19, comprising an essentially circular holder apparatus (13) with a plurality of recesses (13*d*) arranged spaced to one another in the direction of the periphery, with the diameter of the recesses (13*d*) being matched with respect to the shear bodies (7) such that the shear bodies (7) can be fixed in the recesses (13*d*).

21. Kit in accordance with claim 20, characterized in that the recesses (13*d*) are spaced on the holder apparatus (13) such that all shear bodies (7) held are simultaneously insertable into the holder openings (5*c*) of the receiver (5).

22. Kit in accordance with claim 20, characterized in that the recess (13*d*) comprises two circular, overlapping bores (13*b,* 13*c*) of differing diameter, with the centers of the two bores (13*b,* 13*c*) being arranged slightly offset in the direction of the periphery of the holder apparatus (13).

\* \* \* \* \*